United States Patent [19]

Hetz et al.

[11] Patent Number: 5,035,006
[45] Date of Patent: Jul. 30, 1991

[54] CONVERTIBLE MASK, ASCOT AND VISOR GARMENT AND METHOD OF CONVERSION THEREBETWEEN

[75] Inventors: Mary N. Hetz; Bruce J. Brothers, both of Bend, Oreg.

[73] Assignee: Hot Cheeks, Inc., Bend, Oreg.

[21] Appl. No.: 426,873

[22] Filed: Oct. 25, 1989

[51] Int. Cl.⁵ .............................................. A42B 1/04
[52] U.S. Cl. ........................................ 2/209.1; 2/12; 2/203; 2/206
[58] Field of Search ............... 2/209.1, 196, 206, 207, 2/203, 12, 9; 128/206.12, 206.19, 206.28

[56] References Cited

U.S. PATENT DOCUMENTS

| | | | |
|---|---|---|---|
| 766,963 | 8/1904 | Murray | 2/206 |
| 2,070,754 | 2/1937 | Schwartz | 128/206.12 |
| 3,373,447 | 3/1968 | Kim | 2/196 |
| 3,449,766 | 6/1969 | Garber et al. | 2/196 |
| 4,293,958 | 10/1981 | Zauner | 2/209.1 X |
| 4,300,240 | 11/1981 | Edwards | 2/206 |
| 4,351,067 | 9/1982 | Bartels | 2/161 R X |
| 4,392,258 | 7/1983 | O'Neill | 2/209.1 |
| 4,593,417 | 6/1986 | Brown, Jr. et al. | 2/209.1 |
| 4,641,380 | 2/1987 | Epstein | 2/209.1 |

FOREIGN PATENT DOCUMENTS 0833431 4/1960 United Kingdom .................. 2/207

*Primary Examiner*—Peter Nerbun
*Attorney, Agent, or Firm*—Klarquist, Sparkman, Campbell, Leigh & Whinston

[57] ABSTRACT

A garment selectively convertible between several different fashions, such as an ascot, a face and neck mask, and a visor, includes a body or bib portion having a protruding distal edge and opposing side edges. The garment further includes a nose portion having a proximate edge opposite the distal edge, and a breathing vent portion of a foraminous fabric interconnecting the body and nose portions. Two opposing side straps extend outwardly from each of the side edges to secure the garment on a wearer. The side straps may each have a mating portion of a VELCRO hook and eye fabric fastener means attached thereto for releasably interconnecting the straps to secure the garment on a wearer and to provide incremental size adjustment of the garment. Alternatively, the side straps may be permanently interconnected by an elastic insert for resiliently securing the garment on a wearer. The body, nose and strap portions of the garment are preferably formed by inner and outer layers of fabric, with the outer layer being of a water repellant or weather resistant fabric, and the inner layer being a soft fabric, such as a cotton fleece. A method is also provided of converting such a garment between uses as an ascot, a face mask, and a visor.

28 Claims, 3 Drawing Sheets

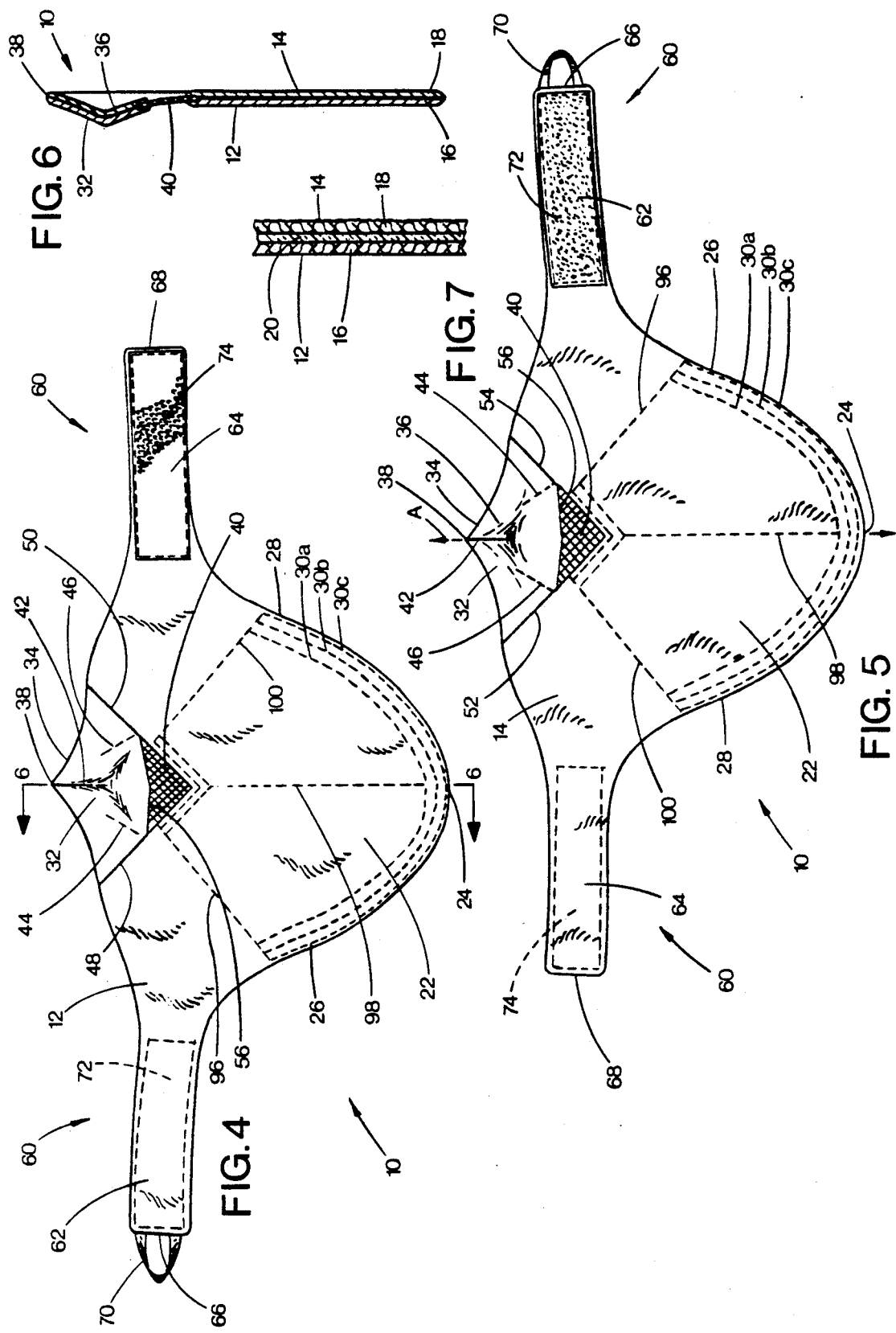

5,035,006

CONVERTIBLE MASK, ASCOT AND VISOR GARMENT AND METHOD OF CONVERSION THEREBETWEEN

BACKGROUND OF THE INVENTION

The present invention relates generally to an article of clothing or a garment, and more particularly to neck warmers, masks, and visors.

Convertible garments have been proposed for selectively covering a wearer's head, face, or neck. For example, U.S. Pat. No. 4,641,380 discloses an article of headwear which is convertible between a hat, a neck warmer and an arm band. A method of converting the article between these uses is also disclosed. The article has a tubular covering of a stretchable knitted fabric with a VELCRO closure at one end of the tube. A slit, which is closeable by a zipper, extends from the VELCRO closeable end of the article approximately halfway to the open end. With the zipper closed and the VELCRO closure open, the article may be rolled and worn around a wearer's arm as an arm band. With the zipper and VELCRO end both closed, the article is used as a hat. With the zipper and VELCRO closure open, the article may be pulled over the head and worn in turtleneck fashion as a neck warmer. In this neck warmer configuration, the hook portion of the VELCRO closure may disadvantageously become entangled in the fabric of a wearer's sweater, shirt or jacket causing damage, or may project through such an undergarment to irritate the wearer's skin.

Another such device is disclosed in U.S. Pat. No. 3,449,766 as a convertible head covering or dickey. The article is of a stretchable knit material having a tubular portion which forms a turtleneck of the dickey, and front and rear portions which extend downwardly from the tubular portion when worn as a dickey. To form a crown portion of the head covering or hat, the front and rear portions are interconnected by a snap and the tubular portion encircles the wearer's head. This article does not provide any protection or covering for a wearer's face.

U.S. Pat. No. 3,373,447 discloses a convertible head and neck enclosing mask and a skull-type hat. The article is of a stretchable knit material having eye holes and a mouth hole therethrough and stretchably conforming to the remaining features of a wearer's head and neck. The face mask has a loop at the top of the crown and a button below the mouth hole. The loop and button are interconnected to cover the eye and mouth holes for use as the skull-type hat.

U.S. Pat. No. 4,593,417 discloses a convertible survival cap having two pair of VELCRO-closeable flaps, one pair for covering a wearer's nose and the other pair for covering the chin. The cap also has a bill portion which extends outward over a wearer's eyes and a rear portion which extends downward to cover the back of a wearer's neck. VELCRO attachments are provided on the outside of the cap to secure the nose and chin flaps in position away from the face. VELCRO attachments are also provided to lift and secure the rear portion away from a wearer's neck so the survival cap may be worn in a baseball cap configuration.

U.S. Pat. No. 4,392,258 discloses a long sleeved T-shirt having a neck opening and a semi-stiff bill projecting downwardly at the rear of the neck opening. The shirt may be worn as a hat with the bill extending over a wearer's eyes and the neck band portion of the shirt encircling the top of a wearer's head. The balance of the shirt body drapes downwardly from the back of a wearer's head and the shirt sleeves may be tied behind the head.

A variety of other garments are known, such as the rubber face mask shown in U.S. Pat. No. 4,300,240.

SUMMARY OF THE INVENTION

It is an overall object of the present invention to provide an improved garment which is useful as a cold weather face and neck mask.

A further object is to provide such a garment which is selectively convertible between an ascot or neck warmer, a face mask and a visor, and to provide a method for converting such a garment between these three different fashions of wear.

Another object of the present invention is to provide a single garment which may be worn indoors or all day long outdoors during outdoor recreational, work or sporting activities, and which may be adjusted to provide for a wearer's comfort during changing weather conditions.

A further object of the present invention is to provide such a garment which comfortably fits on wearers of different sizes.

An additional object of the present invention is to provide such a garment which is incrementally adjustable in size.

A further object of the present invention is to provide such a garment which resiliently maintains a comfortable fit on wearers of different sizes.

Another object of the present invention is to provide such a garment which has a water repellant or weather resistant outer surface, and a soft inner lining which is comfortable when worn against a wearer's skin.

Still another object of the present invention is to provide such a garment which, when worn as a face mask, keeps a wearer's face and neck warm while allowing ease of breathing.

Yet another object of the present invention is to provide such a garment which, when worn as a visor, has a self-supporting brim or bill portion for shielding a wearer's eyes, such as from sunlight.

Still a further object of the present invention is to provide such a garment which may conveniently be hung up from a peg or coat hanger during storage, transportation or drying.

Still a further object of the present invention is to provide a method of converting a single garment between uses as a neck warmer, a face mask and a visor.

According to one aspect of the present invention, a garment includes a body portion having a protruding distal edge and opposing side edges. The garment also includes a nose portion having a proximate edge opposite the distal edge, and a breathing vent portion of a foraminous fabric interconnecting the body and nose portions. The garment also includes securing means adjacent the side edges for securing the garment on a wearer in one of three selectable fashions.

In a first fashion, such a garment may be worn as an ascot or neck warmer, with the securing means extending around a wearer's neck. The body portion drapes downwardly from the fastening means to cover a portion of the wearer's chest.

In a second fashion, the garment may be worn as a face and neck mask, with the securing means extending around a wearer's head. In this second fashion, the nose portion receives the wearer's nose and the breathing vent portion allows ease of breathing. The body portion drapes downwardly from the securing means to cover a portion of the wearer's face and neck.

In a third fashion, the garment may be worn as a visor. In this fashion, the garment is folded approximately parallel to the proximate edge and substantially along the nose portion to form a front band portion of the visor. With the securing means extending from the front band portion around a wearer's head, the body portion extends outwardly from the wearer's head and over the wearer's eyes to form a bill portion of the visor. The bill portion of the visor is adjustable in length from the front band portion to the distal edge by varying the position of the fold along the nose portion.

According to another aspect of the present invention, a multi-purpose apparel accessory is provided which includes an outer layer of a weather resistant fabric, and an inner lining layer of a soft fabric. The inner and outer layers are joined to form a garment having a substantially flat bib portion, a nose portion forming a protruding pocket, and two substantially flat and outwardly projecting strap portions. The joined inner and outer layers have an orifice therethrough, which is located between the nose and bib portions. The strap portions being adapted for securing the apparel accessory on a wearer in a first, second or third fashion.

According to a further aspect of the present invention, a method is provided of converting a garment between uses as a neck warmer, a face mask and a visor. The method includes the steps of providing a garment of a fabric material having a substantially flat bib portion, a nose portion and a breathing vent portion adjacent to the bib portion. The provided garment also includes securing means adjacent the nose and breathing vent portions for securing the garment on a wearer. The method further includes the steps of orienting the bib portion to hang downwardly from the nose portion, and securing the securing means about a wearer's neck when the garment is to be used as an ascot. The method also includes the steps of orienting the bib portion to hang downwardly from the nose portion, of receiving a wearer's nose with the nose portion, and of securing the securing means about a wearer's head when the garment is to be used as a face mask. The method also includes the steps of folding the garment along the nose portion so the securing means and a part of the nose portion serve as a headband portion and the bib portion serves as a bill portion. In a placing step, the bill portion is placed to extend outwardly from a position over a wearer's eyes, while in a securing step, the securing means is secured about a wearer's head when the garment is to be used as a visor.

These and other objects, features and advantages of the present invention will become apparent to those skilled in the art from the following description and drawings.

BRIEF DESCRIPTION OF THE DRAWINGS

FIGS. 4 and 5 are plan views of opposing sides of one form of a garment of the present invention;

FIG. 6 is a cross sectional view taken along lines 6—6 of FIG. 4;

FIG. 7 is an enlarged detailed view of a portion of FIG. 6; and

DETAILED DESCRIPTION

Figure 3:
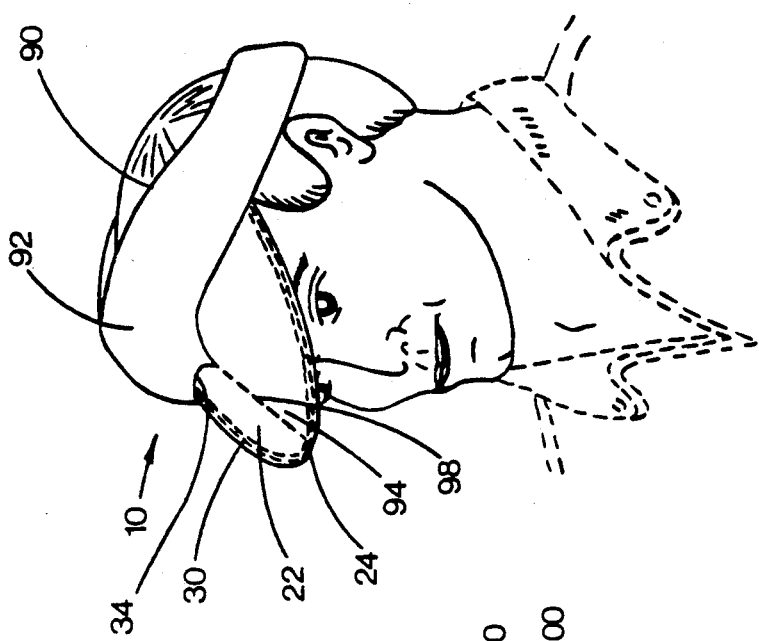
FIGS. 1, 2 and 3 are perspective views of one form of a garment of the present invention when worn by a wearer as a neck warmer, as a face and neck mask, and as a visor, respectively.
Figure 2:
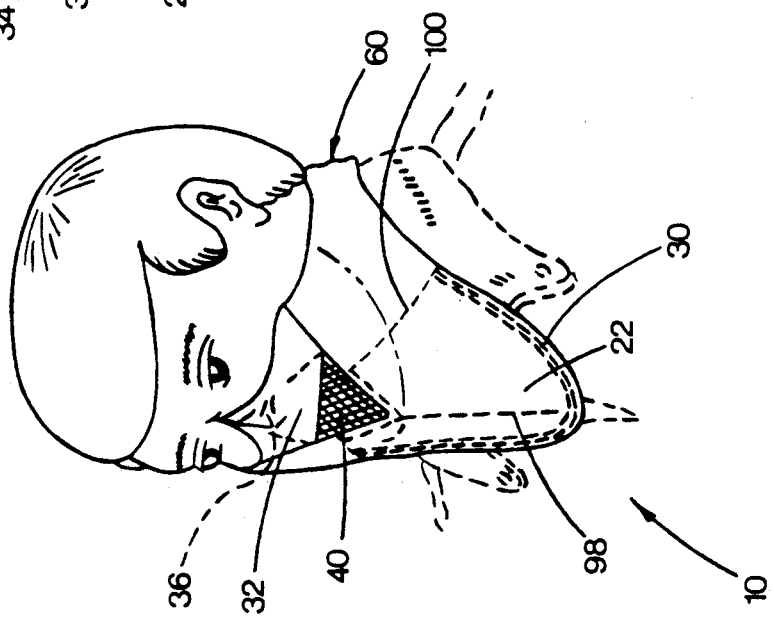
Figure 1:
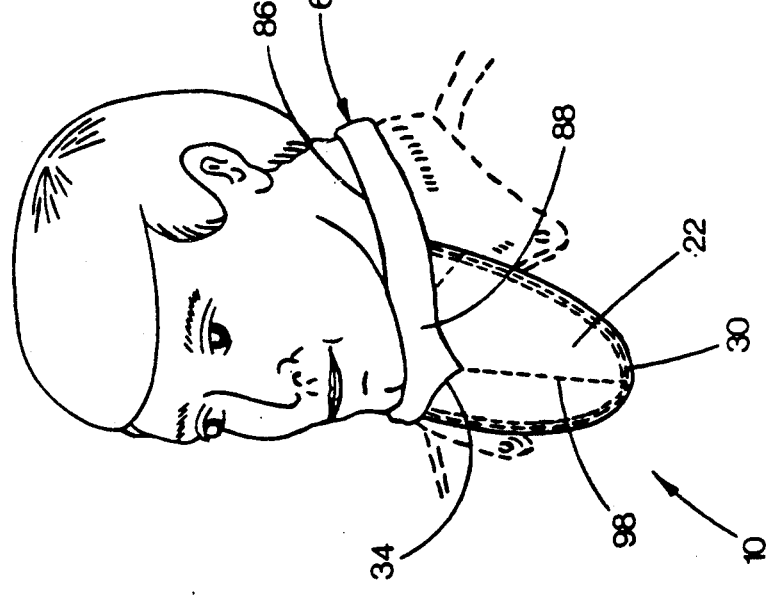

A multi-purpose apparel accessory or garment 10, which is selectively convertible for wearing in at least three different fashions, such as a neck warmer/ascot, a face and neck mask, and a visor, is illustrated on a wearer in FIGS. 1, 2 and 3, respectively. The garment 10 has a first surface 12 shown in FIG. 4, and an opposing second surface 14 shown in FIG. 5. The first surface 12 is preferably formed by a first or outer fabric layer 16, and the second inner surface is preferably formed by a second inner fabric layer 18. The preferred outer fabric layer 16 may be either of a weather-resistant fabric or a water repellent fabric, such as commonly sold under the trademark Gortex. The inner fabric layer 18 is preferably of a soft fabric, such as a flannel or a cotton fleece fabric, which may be comfortably worn against a wearer's skin when the garment is worn as an ascot and as a face and neck mask (see FIGS. 1 and 2).

To provide added warmth if desired, a thermally insulative layer 20, as shown in FIG. 7, may be inserted between the first and second fabric layers 16, 18 in particular regions of the garment or throughout the entirety of the garment as desired. The inner and outer fabric layers 16, 18, and the insulative layer 20 if used, are joined together, such as by threaded stitching or adhesive means, or a combination thereof, to form the garment 10.

Referring now to FIGS. 4 and 5, the garment 10 includes a substantially flat body or bib portion 22 having a protruding distal edge 24 which joins opposing side edges 26, 28, to define an outer edge of the bib portion 22. The sides 26, 28 and the distal edge 24 are illustrated as forming a continuous parabolic-shaped arc, although it is apparent that other shapes, such as triangular, oval, rectangular, or contoured shapes would be suitable. Reinforcement means, such as at least one row, and preferably plural rows of top stitching 30a, 30b and 30c are provided adjacent the distal edge 24 and an adjoining portion of each side edge 26, 28, for stiffening the bib portion outer edge.

The garment 10 also has a nose portion 32 which has a proximate edge 34 opposite the bib portion distal edge 24. As shown in FIG. 6, the nose portion 32 preferably forms a protruding nose-shaped pocket or recess 36 which receives a wearer's nose when worn as a mask (see in FIG. 2). The illustrated proximate edge 34 includes an apex 38 which extends upwardly along the bridge of a wearer's nose to provide warmth when worn as a mask. Located between the nose and bib portions 32 and 22, the joined inner and outer layers 16, 18 have an orifice therethrough forming a breathing vent portion 40. Preferably the breathing vent portion is of a foraminous fabric which interconnects the nose and body portions. The foraminous fabric may be any type of mesh or net fabric, but is preferably constructed of a stretchable foraminous fabric. To provide additional warmth for the wearer of the garment as a mask, two or more such layers of the foraminous fabric may be used.

While a stretchable fabric may be used to form the nose portion 32 of the garment, the illustrated embodiment uses a tightly woven, non-stretchable fabric as the outer layer 16. The nose portion inner layer 18 may e of either a stretchable or a non-stretchable fabric. However, using at least one of the inner or outer fabric layers 16 or 18 as non-stretchable, advantageously provides for wearer comfort, in that the wearer's nose is not required to deform the fabric to form a nose-receiving recess.

In the illustrated embodiment, using a non-stretchable outer fabric layer 16, the nose pocket 36 is formed by removing a V-shaped portion of material symmetrically along a longitudinal axis A, coincident with view line 6—6 of FIG. 4 and as shown in FIG. 5. The upper edges of the removed V-shaped portion of material are located symmetrically about axis A along the proximate edge 34, and the apex of the V-shaped portion extends to the approximate point where the end a wearer's nose would be located. The two edges remaining in the garment after removal of this V-shaped piece of material are then joined together, such as by stitching along line 42. Alternatively, instead of removing the V-shaped piece of material, a gather may be made in the inner and outer fabric layers 16, 18, with the excess material sandwiched and sewn between the layers 16, 18. Two additional rows of top stitching 44, 46 may be added to further define the nose pocket 36. Top stitching rows 44, 46 also secure the inner and outer layers in this region to prevent movement relative to one another.

To aid in constructing the garment, and to enhance the aesthetic appeal of the garment, the body portion 22 and the nose portion 32 may be of different pieces of fabric, and of contrasting colors. The outer fabric layer 16 body and nose portions are joined by stitching along lines 48 and 50 (see FIG. 4). Similarly, the nose and bib portions 32, 22 of the inner fabric layer 18 may be of different pieces of fabric and stitched together along lines 52 and 54 (see FIG. 5).

In the illustrated embodiment, the breathing vent portion 40 is generally triangular in shape, being defined by attachment to a distal edge 56 of the nose portion 32, and by attachment to the bib portion 22 along lines 48, 50 of the outer layer 16, and along lines 52, 54 of inner layer 18. As shown in FIGS. 4 and 5, the respective lines 48, 50 and 52, 54 meet to form a lower angle of the triangular breathing vent portion 40. Referring to FIG. 6, the outer edges of the foraminous fabric surrounding the breathing vent portion 40 are sandwiched between the inner and outer layers 16, 18 of the nose and bib portions 32, 22.

The garment also has securing means 60 adjacent the nose and breathing vent portions 32, 40 and bib side edges 26, 28 for securing the garment on a wearer. In the embodiment of FIGS. 4 and 5, the securing means 60 comprises two substantially flat and outwardly projecting opposing side strap portions 62, 64 extending outwardly from the respective bib side edges 26, 28. Each side strap 62, 64 has a respective distal end 66, 68. Hanging means, such as a loop 70, may be attached to one of the side strap distal ends, such as end 66, for suspending the garment 10 from the loop. The loop 70 may be of a fabric or cord, and may be sandwiched between the inner and outer layers 16, 18 of the strap portion and stitched in place.

In the embodiment of FIGS. 4 and 5, the securing means 60 includes fastening or closure means for securing the strap portions 62, 64 to one another and for releasably securing the garment 10 on a wearer. The closure or fastening means may be buttons and buttonholes, snaps, or the like, but the preferred closure means comprises hook and eye fabric fastener means, such as that sold under the trademark VELCRO. Each strap portion 62, 64 has a mating portion of the VELCRO fastener means attached thereto, such as by stitching.

In the illustrated embodiment, a loop or eye portion 72 of the VELCRO is sewn to the inner surface 14 of side strap 62. A hook portion 74 of the VELCRO closure means is sewn to the outer surface 12 of side strap 64. When worn as a face mask (see FIG. 2), with the soft inner fabric layer 18 placed against the wearer's face, the rougher VELCRO hook portion 74 is directed outwardly away from a wearer's head and hair, and only the softer VELCRO eye or loop portion 72 is oriented toward a wearer's skin or hair. This manner of attachment provides a more comfortable garment to wear. Additionally, this orientation of the VELCRO and loop 70 leaves the loop accessible when worn to aid in releasing the VELCRO and removing the garment. Thus the VELCRO closure means provides a quickly releasable interconnection of the strap portions.

Furthermore, the VELCRO fastener means further provide for incremental size adjustment of the accessory so it may fit a variety of wearers of different sizes. Also the garment may be incrementally adjusted to accommodate the comfort of the wearer.

Figure 8:
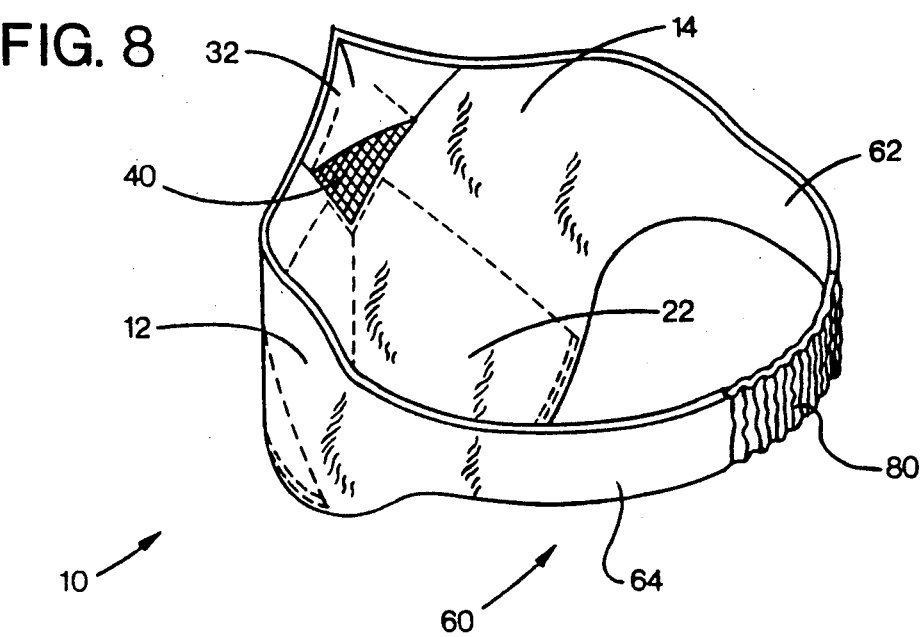
FIGS. 8 and 9 are perspective views of two alternate forms of the present invention.

FIG. 8 illustrates an alternate embodiment of the securing means 60 comprising resilient means extending outwardly from and interconnecting each of the side edges 26 and 28, for resiliently securing the garment on a wearer. In this illustrated embodiment, an elastic portion 80 interconnects the distal ends 66, 68 of the respective side straps 62, 64. The side straps 62, 64 are shorter in this embodiment than in that of FIGS. 4 and 5, due to the presence of the elastic insert 80 in FIG. 8, and due to the need for overlapping the straps in the embodiment of FIGS. 4 and 5. The elastic insert 80 may be sandwiched between the inner and outer layers 16, 18 of the strap portions 62, 64 and secured in place by stitching.

Figure 9:
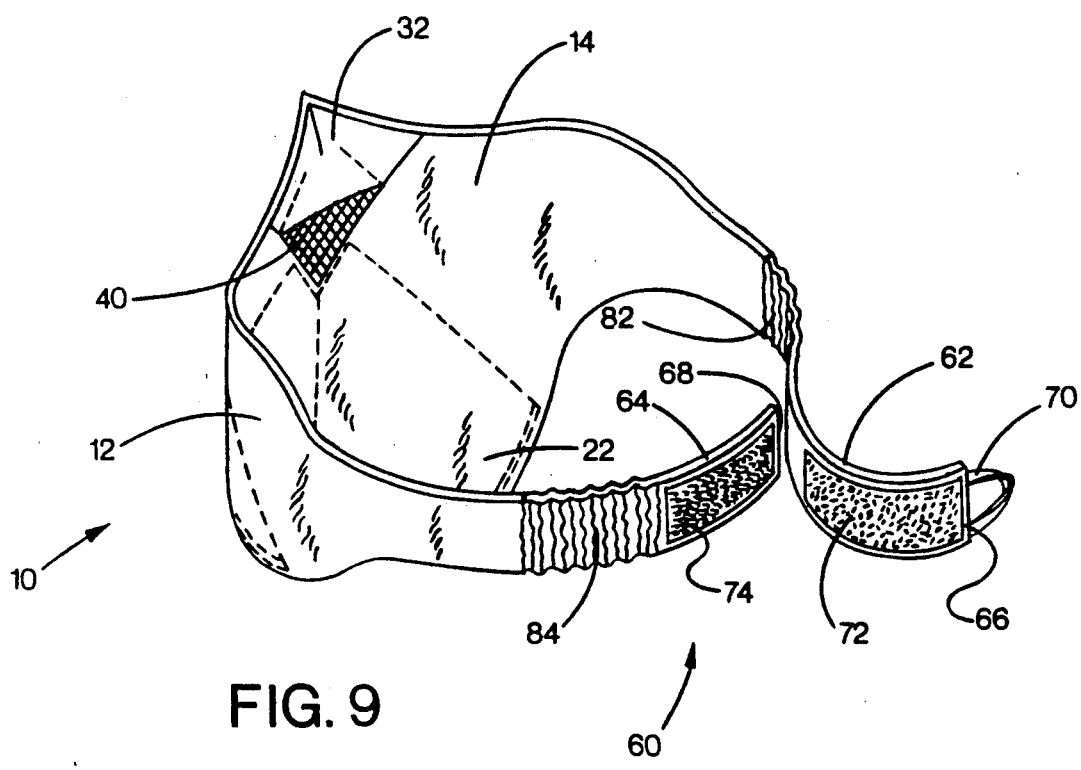

FIG. 9 illustrates a third embodiment of the securing means 60. Here, the garment 10 includes side strap portions 62, 64 having mating VELCRO portions secured adjacent the respective distal ends 66, 68 of the side straps. The garment 10 further includes at least one of the side strap portions also having resilient means. In the illustrated embodiment, the resilient means comprises the side straps 62, 64 each having respective elastic inserts 82, 84. The VELCRO and elastic inserts in this embodiment may be attached to the side straps as described above for the respective embodiments of FIGS. 4, 5 and of FIG. 8.

Thusly constructed, the garment 10 may be worn in any one of three fashions. Referring to FIG. 1, the garment 10 may be worn as an ascot or neck warmer, with the securing means extending around a wearer's neck. The bib or body portion 22 drapes downwardly from the securing means 60 to cover a portion of the wearer's chest. In the fashion as illustrated in FIG. 1, the garment 10 may be folded along fold 86 approximately parallel to the nose portion proximate edge 34 to define a front band portion 88 of the ascot. The securing means extends from the front band portion 88 around the wearer's neck to secure the ascot in place. If the embodiments of FIGS. 4 and 5 or FIG. 9 are used, the straps 62, 64 extend around the wearer's neck to engage the VELCRO closure means. Alternatively, if the embodiment of FIG. 8 is used, or that FIG. 9 with the VELCRO closure engaged, the garment may be pulled down over the head of a wearer to seat around the wearer's neck.

Referring to FIG. 2, the garment 10 may be worn in a second fashion as a face mask, or as a face and neck mask, with the securing means 60 extending around a wearer's neck. The nose pocket 36 of the nose portion 32 receives a wearer's nose, while the breathing vent portion 40 allows the wearer ease of breathing. The bib or body portion 22 drapes downwardly from the securing means to cover a portion of the wearer's face and neck. The mask may be put on by the wearer in a manner similar to that described for the ascot of FIG. 1. When the garment is worn as a neck warmer or mask, the bib 22 may be worn outside the wearer's shirt and coat or tucked in. In windy conditions, it is preferred that the bib 22 extend between the wearer's coat and chest to provide a seal.

Referring to FIG. 3, the garment 10 may be worn as a visor. In this fashion, the garment 10 is folded along fold 90, which is approximately parallel to the proximate edge 34 and substantially along the nose portion 32, to form a front band portion 92 of the visor. Thus a headband portion of the visor is formed by the front band portion 92 and the securing means 60. The bib or body portion 22 of the visor extends outwardly from the wearer's head and over the wearer's eyes to form a bill portion 94 of the visor. By varying the position of the fold 90, the length of the bill portion 94 from the front band portion 92 to the distal edge 24 may be adjusted. In addition to the top stitching 30, additional stitching may be provided in the bib portion 22 to further reinforce and stiffen the bill 94. Such additional reinforcing and stiffening stitching, such as top stitching lines 96, 98 and 100, may extend from an area adjacent the breathing vent portion to the top stitching rows 30.

In a further aspect of the invention, a method is provided of converting a garment 10 between uses as an ascot, a face mask and a visor (see respective FIGS. 1, 2 and 3). This method includes a step of providing a garment 10 of a fabric material comprising a substantially flat bib portion 22, a nose portion 32, and a breathing vent portion 40 adjacent to the bib portion. The providing step further includes providing a garment 10 having securing means 60 adjacent the nose and breathing vent portions 32, 40 for securing the garment on a wearer. The method also includes the steps of orienting the bib portion 22 to hang downwardly from the nose portion 32, receiving a wearer's nose with the nose portion 32, and securing the securing means 60 about a wearer's head when the garment is to be used as a face mask, as shown in FIG. 2. This method also includes the step of folding the garment 10 along the nose portion 32 so the securing means 60 and a part of the nose portion 32 serve as a headband portion 92, while the bib portion 22 serves as a bill portion 94, when the garment is to be used as a visor, as shown in FIG. 3. In a placing step, the bill portion 94 is placed to extend outwardly from a position over a wearer's eyes, and in a securing step the securing means 60 are secured about a wearer's head when the garment is to be used as a visor.

The above method may be modified, wherein the providing step further includes the step of providing a garment 10 having a breathing vent portion 40 of a foraminous material. Furthermore, the providing step may comprise the step of providing a garment 10 which has securing means 60 comprising fastening means. Such fastening means may include two substantially flat opposing strap portion 62, 64 extending outwardly from the nose and breathing vent portions 32, 40. This fastening means also includes each strap portion 62, 64 having a mating portion of hook and eye fabric fastener means 72, 74 respectively, for releasably securing the garment on a wearer. With such a providing step including fastening means, the method may further include the step of incrementally adjusting the size of the garment 10 by releasing and interconnecting the mating portions 72, 74 of the VELCRO hook and eye fabric fastener means.

In the above method, a further step may be included for use of the garment as an ascot. This additional step is one of folding the garment 10 along fold 86 of the nose portion 32, so the securing means 60 and a part of the nose portion 32 serve as a neck band portion 88 of the ascot.

The above method of converting a garment 10 may further include a modified folding step for use of the garment as a visor. This modified folding step comprises the step of incrementally adjusting the length of the bill portion 94 by varying the position of the resulting fold 90 along the nose portion 32.

Having illustrated and described the principles of the invention with respect to a preferred embodiment and alternate embodiments, it should be apparent to those skilled in the art that the invention may be modified in arrangement and detail without departing from such principles. For example, although inner and outer fabric layers 16 and 18 are illustrated, the garment may be suitably constructed from a single layer of material with the edges of the various fabric pieces joined by overlapping and stitching, as opposed to being sandwiched between the inner and outer layers. It is, therefore, intended that any and all such modifications be covered by the following claims.

We claim:

1. A garment selectively convertible between an ascot, a face and neck mask, and a visor, comprising:
   a body portion having a protruding distal edge and opposing side edges, the body portion being of a size and shape sufficient to interchangeably form a bill portion of a visor, a draping portion of an ascot, and a neck portion of a mask;
   a nose portion having a proximate edge opposite the distal edge;
   a breathing vent portion of a foraminous fabric interconnecting the body and nose portions, the breathing vent portion being located and shaped such that the breathing vent portion is exposed when the garment is worn as a mask and covered when the garment is worn as an ascot and as a visor; and
   securing means adjacent the side edges for securing the garment on a wearer's head, about a wearer's neck, and over a wearer's face;
   the body portion, nose portion, breathing vent portion and securing means being positioned in relation to each other such that, in a first fashion, with the garment worn as an ascot, the securing means extends around a wearer's neck and the body portion drapes downwardly from the securing means to cover a portion of the wearer's chest; in a second fashion, with the garment worn as a face and neck mask, the securing means extends around a wearer's head, the nose portion receives a wearer's nose and the breathing vent portion allows ease of breathing, and the body portion drapes downwardly from the securing means to cover a portion of the wearer's face and neck; and in a third fashion, with the garment worn as a visor, the garment is folded approximately parallel to the proximate edge and substantially along the nose portion to form a front band portion of the visor, the securing means extends from the front band portion around a wearer's head, and the body portion extends outwardly from the wearer's head and over the wearer's eyes to form a bill portion of the visor, with the bill portion being adjustable in length from the front band portion to the distal edge depending on the position of the fold along the nose portion.

2. A garment according to claim 1 wherein the nose portion forms a nose-shaped pocket which receives the wearer's nose.

3. A garment according to claim 1 wherein the body and nose portions are each of a fabric material, and the garment has opposing first and second surfaces.

4. A garment according to claim 3 wherein the first surface is of a water repellant fabric, and the second surface is of a soft fabric which may be worn against a wearer's skin in the first and second fashions.

5. A garment according to claim 2 wherein the first surface is of a weather resistant fabric, the second surface is of a soft fleece fabric, and the garment further includes a thermally insulative layer sandwiched between the weather resistant fabric and the soft fleece fabric.

6. A garment according to claim 1 wherein in the first fashion when the garment is worn as an ascot, the garment is folded approximately parallel to the proximate edge along the nose portion to form a front band portion of the ascot, and the securing means extend from the front band portion around the wearer's neck.

7. A garment according to claim 1 wherein the securing means comprises resilient means extending outwardly from and interconnecting each of the side edges for resiliently securing the garment on a wearer.

8. A garment according to claim 1 wherein the securing means comprises fastening means for releasably securing the garment on a wearer.

9. A garment according to claim 8 wherein the fastening means comprises two opposing strap portions of a fabric material, with each strap portion extending outwardly from one of the side edges.

10. A garment according to claim 9 wherein:
each strap portion has hook and eye fabric fastener means attached thereto for releasably interconnecting the strap portions and for providing incremental size adjustment of the garment; and
at least one of the strap portions includes biasing means for urging the strap portions to snugly secure the garment on a wearer.

11. A garment according to claim 9 wherein each strap portion has a distal end, and the garment further includes a loop attached to the distal end of one of the strap portions, whereby the garment may be suspended from the loop.

12. A garment according to claim 1 wherein the garment further includes reinforcement means adjacent the protruding distal edge and an adjoining portion of each side edge for stiffening the bill portion of the visor so that the bill is self-supporting when the garment is worn in the third fashion.

13. A method of converting a garment between uses as an ascot, a face mask, and a visor, comprising the steps of:
providing a garment of a fabric material comprising:
(a) a substantially flat bib portion,
(b) a nose portion and a breathing vent portion adjacent the bib portion, and
(c) securing means adjacent the nose and breathing vent portions for securing the garment on a wearer;
orienting the bib portion to hang downwardly from the nose portion and securing the securing means about a wearer's neck when the garment is to be used as an ascot;
orienting the bib portion to hang downwardly from the nose portion, receiving a wearer's nose with the nose portion, and securing the securing means about a wearer's head when the garment is to be used as a face mask;
folding the garment along the nose portion so the securing means and a part of the nose portion serve as a headband portion and the bib portion serves as a bill portion, placing the bill portion to extend outwardly from a position over a wearer's eyes, and securing the securing means about a wearer's head when the garment is to be used as a visor.

14. A method of converting a garment according to claim 13 wherein the providing step further comprises the step of providing a garment having a breathing vent portion of a foraminous material.

15. A method of converting a garment according to claim 14 wherein:
the providing step further comprises the step of providing a garment which has securing means comprising fastening means including two substantially flat opposing strap portions extending outwardly from the nose and breathing vent portions, with each strap portion having a mating portion of hook and eye fabric fastener means for releasably securing the garment on a wearer; and
the method further comprises the step of incrementally adjusting the size of the garment by releasing and interconnecting the mating portions of the hook and eye fabric fastener means.

16. A method of converting a garment according to claim 13 wherein between the orienting and securing steps for use of the garment as an ascot, the method further includes the step of folding the garment along the nose portion so the securing means and a part of the nose portion serve as a neck band portion of the ascot.

17. A method of converting a garment according to claim 14 wherein the folding step for use of the garment as a visor further comprises the step of incrementally adjusting the length of the bill portion by varying the position of the resulting fold along the nose portion.

18. A multi-purpose apparel accessory comprising an outer layer of a weather resistant fabric and an inner lining layer of a soft fabric, the inner and outer layers being joined to form a garment having a substantially flat bib portion of a size and shape sufficient to interchangeably form a bill portion of a visor, a draping portion of an ascot, and a neck portion of a mask, a nose portion forming a protruding pocket, and two substantially flat and outwardly projecting opposing strap portions, the strap portions being adapted for interchangeably securing the apparel accessory on a wearer in a first fashion about a wearer's neck, in a second fashion over a wearer's face, and in a third fashion on a wearer's head, the joined inner and outer layers having an orifice therethrough located between the nose and bib portions, the orifice being located and shaped such that it is exposed when the apparel accessory is worn in the second fashion and covered when worn in the first and third fashions, the strap portions being adapted for securing the apparel accessory on a wearer when the apparel accessory is worn in the first, second and third fashions.

19. A multi-purpose apparel accessory according to claim 19 further comprising closure means for securing the strap portions to one another.

20. A multi-purpose apparel accessory according to claim 20 wherein:
the first fashion comprises wearing the accessory as an ascot, with the straps extending around a wearer's neck to engage the closure means, and the bib portion draping downwardly to cover a portion of the wearer's chest;
the second fashion comprises wearing the accessory as a face and neck mask, with the straps extending around a wearer's head to engage the closure means, the nose portion pocket receiving the wearer's nose, and the bib portion covering a portion of the wearer's face and neck; and
the third fashion comprises wearing the accessory as a visor, with the accessory folded so the straps and nose portion serve as a headband portion of the visor, with the straps extending around the wearer's head to engage the closure means, and the bib portion serving as a bill portion of the visor, whereby the bill portion is adjustable in length by varying the position of the fold.

21. A multi-purpose apparel accessory according to claim 19 wherein the closure means comprises hook and eye fabric fastener means for releasably interconnecting the strap portions and for providing incremental size adjustment of the accessory.

22. A multi-purpose apparel accessory according to claim 18 wherein the orifice comprises a foraminous fabric layer to allow ease of breathing and ventilation while maintaining a wearer's warmth.

23. A multi-purpose apparel accessory according to claim 18 further including a thermally insulative layer sandwiched between the inner and outer layers.

24. A multi-purpose apparel accessory according to claim 18 wherein the bib portion has an outer edge with at least one row of top-stitching along the outer edge, whereby the visor bill is self-supporting when the garment is worn in the third fashion.

25. A neck warmer garment comprising:
a body portion having a protruding distal edge and opposing side edges;
a nose portion having a proximate edge opposite the distal edge; and
securing means adjacent the side edges for securing the garment on a wearer;
the garment being folded approximately parallel to the proximate edge and substantially along the nose portion to form a front band portion of the neck warmer, with the securing means extending from the front band portion around a wearer's neck, the body portion draping downwardly from the securing means to cover a portion of the wearer's chest.

26. The garment of claim 25 wherein:
the body portion has opposed first and second surfaces;
the nose portion has opposed first and second surfaces contiguous, respectively, to the first and second surfaces of the body portion; and
the first surface of the nose portion faces the first surface of the body portion of the folded garment.

27. A visor garment comprising:
a body portion having a protruding distal edge and opposing side edges;
a nose portion having a proximate edge opposite the distal edge; and
securing means adjacent the side edges for securing the garment on a wearer;
the garment being folded approximately parallel to the proximate edge and substantially along the nose portion to form a front band portion of the visor, with the securing means extending from the front band portion around a wearer's head, the body portion extends outwardly from the wearer's head and over the wearer's eyes to form a bill portion of the visor, whereby the bill portion is adjustable in length from the front band portion to the distal edge by varying the position of the fold along the nose portion.

28. The garment of claim 27 wherein:
the body portion has opposed first and second surfaces;
the nose portion has opposed first and second surfaces contiguous, respectively, to the first and second surfaces of the body portion; and
the first surface of the nose portion faces the first surface of the body portion of the folded garment.

* * * * *

UNITED STATES PATENT AND TRADEMARK OFFICE
CERTIFICATE OF CORRECTION

PATENT NO. : 5,035,006

DATED : July 30, 1991

INVENTOR(S) : MARY N. HETZ AND BRUCE J. BROTHERS

It is certified that error appears in the above-identified patent and that said Letters Patent is hereby corrected as shown below:

```
Column 10, line 25, "14" should be --13--.

Column 10, line 45, "14" should be --13--.

Column 11, line 4, "19" should be --18--.

Column 11, line 7, "20" should be --19--.
```

Signed and Sealed this

Thirteenth Day of April, 1993

*Attest:*

STEPHEN G. KUNIN

*Attesting Officer*   Acting Commissioner of Patents and Trademarks